(12) United States Patent
Fram et al.

(10) Patent No.: US 7,885,440 B2
(45) Date of Patent: Feb. 8, 2011

(54) SYSTEMS AND METHODS FOR INTERLEAVING SERIES OF MEDICAL IMAGES

(75) Inventors: Evan K. Fram, Paradise Valley, AZ (US); Murray A. Reicher, Rancho Santa Fe, CA (US); Steven M. Greim, Oceanside, CA (US); John J. Schumacher, San Diego, CA (US)

(73) Assignee: DR Systems, Inc., San Diego, CA (US)

( * ) Notice: Subject to any disclaimer, the term of this patent is extended or adjusted under 35 U.S.C. 154(b) by 1193 days.

(21) Appl. No.: 11/268,261

(22) Filed: Nov. 3, 2005

(65) Prior Publication Data

US 2006/0093198 A1  May 4, 2006

Related U.S. Application Data

(60) Provisional application No. 60/625,690, filed on Nov. 4, 2004.

(51) Int. Cl.
  *G06K 9/00* (2006.01)
  *G06K 9/36* (2006.01)
  *G06K 9/03* (2006.01)

(52) U.S. Cl. .................. 382/128; 382/276; 382/309; 710/65

(58) Field of Classification Search ......... 382/128–132, 382/155–161, 276, 282, 284, 309; 710/65
  See application file for complete search history.

(56) References Cited

U.S. PATENT DOCUMENTS

| | | | | |
|---|---|---|---|---|
| 4,672,683 A | * | 6/1987 | Matsueda | 382/305 |
| 5,123,056 A | | 6/1992 | Wilson | |
| 5,431,161 A | * | 7/1995 | Ryals et al. | 600/425 |
| 5,452,416 A | * | 9/1995 | Hilton et al. | 715/783 |
| 5,734,915 A | | 3/1998 | Roewer | |
| 5,740,267 A | | 4/1998 | Echerer et al. | |
| 5,852,646 A | * | 12/1998 | Klotz et al. | 378/8 |
| 5,926,568 A | * | 7/1999 | Chaney et al. | 382/217 |

(Continued)

OTHER PUBLICATIONS

Supplemental Notice of Allowability (U.S. Appl. No. 11/265,978) dated May 3, 2010.*

(Continued)

*Primary Examiner*—Bhavesh M Mehta
*Assistant Examiner*—Mia M Thomas
(74) *Attorney, Agent, or Firm*—Knobbe, Martens, Olson & Bear, LLP

(57) ABSTRACT

After selecting two or more image series for comparison, images of the image series are interleaved so that they are alternatively displayed in a comparison pane on a display device. In one embodiment, after one or more image series are selected for comparison, an interleaved image series is created containing each of the images of the one or more selected image series, or, alternatively, the interleaved image series comprises links to the images arranged in the interleaved pattern. If differences exist in the images of the multiple image series, these differences may be more easily detectable as the display device cycles between the images. Comparison of images in an interleaved image series may be more advantageous if the images of each selected image series are of a common anatomical area, common image size, and the images are in the same order.

31 Claims, 9 Drawing Sheets

U.S. PATENT DOCUMENTS

| | | | |
|---|---|---|---|
| 5,954,650 A | 9/1999 | Saito et al. | |
| 5,976,088 A | 11/1999 | Urbano et al. | |
| 5,987,345 A | 11/1999 | Engelmann et al. | |
| 5,995,644 A | 11/1999 | Lai et al. | |
| 6,115,486 A | 9/2000 | Cantoni | |
| 6,151,581 A | 11/2000 | Kraftson et al. | |
| 6,175,643 B1 | 1/2001 | Lai et al. | |
| 6,185,320 B1 | 2/2001 | Bick et al. | |
| 6,304,667 B1* | 10/2001 | Reitano | 382/128 |
| 6,347,329 B1* | 2/2002 | Evans | 709/202 |
| 6,351,547 B1 | 2/2002 | Johnson et al. | |
| 6,424,996 B1 | 7/2002 | Killcommons et al. | |
| 6,463,169 B1 | 10/2002 | Ino et al. | |
| 6,532,299 B1* | 3/2003 | Sachdeva et al. | 382/128 |
| 6,532,311 B1 | 3/2003 | Pritt | |
| 6,556,695 B1 | 4/2003 | Packer et al. | |
| 6,563,950 B1 | 5/2003 | Wiskott et al. | |
| 6,574,629 B1* | 6/2003 | Cooke et al. | 1/1 |
| 6,577,753 B2 | 6/2003 | Ogawa | |
| 6,603,494 B1 | 8/2003 | Banks et al. | |
| 6,630,937 B2* | 10/2003 | Kallergi et al. | 345/619 |
| 6,678,764 B2 | 1/2004 | Parvulescu et al. | |
| 6,697,506 B1 | 2/2004 | Oian et al. | |
| 6,775,402 B2 | 8/2004 | Bacus et al. | |
| 6,778,689 B1 | 8/2004 | Aksit et al. | |
| 6,820,100 B2 | 11/2004 | Funahashi | |
| 6,829,377 B2* | 12/2004 | Milioto | 382/128 |
| 6,864,794 B2* | 3/2005 | Betz | 340/573.1 |
| 6,886,133 B2 | 4/2005 | Bailey et al. | |
| 6,891,920 B1* | 5/2005 | Minyard et al. | 378/37 |
| 6,917,696 B2 | 7/2005 | Soenksen | |
| 6,996,205 B2 | 2/2006 | Capolunghi et al. | |
| 7,022,073 B2 | 4/2006 | Fan et al. | |
| 7,027,633 B2 | 4/2006 | Foran et al. | |
| 7,031,846 B2 | 4/2006 | Kaushikkar et al. | |
| 7,043,474 B2 | 5/2006 | Mojsilovic | |
| 7,050,620 B2 | 5/2006 | Heckman | |
| 7,092,572 B2 | 8/2006 | Huang et al. | |
| 7,103,205 B2* | 9/2006 | Wang et al. | 382/132 |
| 7,106,479 B2* | 9/2006 | Roy et al. | 358/3.27 |
| 7,110,616 B2* | 9/2006 | Ditt et al. | 382/284 |
| 7,155,043 B2* | 12/2006 | Daw | 382/128 |
| 7,170,532 B2* | 1/2007 | Sako | 345/637 |
| 7,174,054 B2 | 2/2007 | Manber et al. | |
| 7,209,149 B2* | 4/2007 | Jogo | 345/622 |
| 7,212,661 B2 | 5/2007 | Samara et | |
| 7,218,763 B2 | 5/2007 | Belykh et al. | |
| 7,224,852 B2* | 5/2007 | Lipton et al. | 382/294 |
| 7,263,710 B1* | 8/2007 | Hummel et al. | 725/86 |
| 7,272,610 B2* | 9/2007 | Torres | 1/1 |
| 7,412,111 B2* | 8/2008 | Battle et al. | 382/284 |
| 7,450,747 B2* | 11/2008 | Jabri et al. | 382/132 |
| 7,526,114 B2* | 4/2009 | Xia et al. | 382/128 |
| 7,545,965 B2* | 6/2009 | Suzuki et al. | 382/128 |
| 7,583,861 B2* | 9/2009 | Hanna et al. | 382/305 |
| 7,613,335 B2* | 11/2009 | McLennan et al. | 382/128 |
| 7,634,121 B2 | 12/2009 | Novatzky et al. | |
| 7,636,413 B2* | 12/2009 | Toth | 378/4 |
| 7,660,488 B2* | 2/2010 | Reicher et al. | 382/299 |
| 7,787,672 B2 | 8/2010 | Reicher et al. | |
| 2002/0016718 A1* | 2/2002 | Rothschild et al. | 705/2 |
| 2002/0021828 A1 | 2/2002 | Papier et al. | |
| 2002/0044696 A1* | 4/2002 | Sirohey et al. | 382/240 |
| 2002/0081039 A1 | 6/2002 | Funahashi | |
| 2002/0091659 A1* | 7/2002 | Beaulieu et al. | 706/62 |
| 2002/0103827 A1 | 8/2002 | Sesek | |
| 2002/0106119 A1 | 8/2002 | Foran et al. | |
| 2002/0110285 A1 | 8/2002 | Wang et al. | |
| 2002/0164063 A1 | 11/2002 | Heckman | |
| 2002/0188637 A1* | 12/2002 | Bailey et al. | 707/530 |
| 2003/0028402 A1 | 2/2003 | Ulrich et al. | |
| 2003/0036087 A1 | 2/2003 | Kaushikkar et al. | |
| 2003/0053668 A1* | 3/2003 | Ditt et al. | 382/128 |
| 2003/0115083 A1 | 6/2003 | Masarie et al. | |
| 2003/0123717 A1 | 7/2003 | Bacus et al. | |
| 2003/0185446 A1 | 10/2003 | Huang et al. | |
| 2003/0195416 A1* | 10/2003 | Toth | 600/427 |
| 2004/0008900 A1* | 1/2004 | Jabri et al. | 382/254 |
| 2004/0024303 A1* | 2/2004 | Banks et al. | 600/407 |
| 2004/0068170 A1* | 4/2004 | Wang et al. | 600/407 |
| 2004/0086163 A1 | 5/2004 | Moriyama et al. | |
| 2004/0101191 A1 | 5/2004 | Seul et al. | |
| 2004/0141661 A1 | 7/2004 | Hanna et al. | |
| 2004/0151374 A1 | 8/2004 | Lipton et al. | |
| 2004/0161139 A1* | 8/2004 | Samara et al. | 382/131 |
| 2004/0161164 A1 | 8/2004 | Dewaele | |
| 2004/0165791 A1 | 8/2004 | Kaltanji | |
| 2004/0170312 A1 | 9/2004 | Soenksen | |
| 2004/0197015 A1* | 10/2004 | Fan et al. | 382/128 |
| 2004/0243435 A1 | 12/2004 | Williams | |
| 2004/0254816 A1 | 12/2004 | Myers | |
| 2004/0264753 A1 | 12/2004 | Capolunghi et al. | |
| 2005/0027570 A1 | 2/2005 | Maier et al. | |
| 2005/0036068 A1 | 2/2005 | McLennan et al. | |
| 2005/0043970 A1 | 2/2005 | Hsieh | |
| 2005/0063612 A1 | 3/2005 | Manber et al. | |
| 2005/0065424 A1 | 3/2005 | Shah et al. | |
| 2005/0114178 A1 | 5/2005 | Krishnamurthy et al. | |
| 2005/0114179 A1 | 5/2005 | Brackett et al. | |
| 2005/0114283 A1 | 5/2005 | Pearson et al. | |
| 2005/0184988 A1* | 8/2005 | Yanof et al. | 345/424 |
| 2005/0197860 A1* | 9/2005 | Joffe et al. | 705/2 |
| 2005/0273009 A1 | 12/2005 | Deischinger et al. | |
| 2006/0093199 A1* | 5/2006 | Fram et al. | 382/128 |
| 2006/0093207 A1* | 5/2006 | Reicher et al. | 382/156 |
| 2006/0095423 A1* | 5/2006 | Reicher et al. | 707/3 |
| 2006/0095426 A1* | 5/2006 | Takachio et al. | 707/4 |
| 2006/0106642 A1* | 5/2006 | Reicher et al. | 705/2 |
| 2006/0111941 A1 | 5/2006 | Blom | |
| 2006/0239573 A1* | 10/2006 | Novatzky et al. | 382/239 |
| 2007/0050701 A1* | 3/2007 | El Emam et al. | 715/505 |
| 2007/0055550 A1* | 3/2007 | Courtney et al. | 705/3 |
| 2007/0067124 A1* | 3/2007 | Kimpe et al. | 702/67 |
| 2007/0073556 A1 | 3/2007 | Lau et al. | |
| 2007/0174079 A1 | 7/2007 | Kraus | |
| 2007/0239481 A1 | 10/2007 | DiSilvestro et al. | |
| 2008/0103828 A1* | 5/2008 | Squilla et al. | 705/3 |
| 2010/0138239 A1* | 6/2010 | Reicher et al. | 705/3 |
| 2010/0201714 A1 | 8/2010 | Reicher | |

OTHER PUBLICATIONS

Crowley, Rebecca et al., *Development of Visual Diagnostic Expertise in Pathology: an Information-processing Study*, Jan. 2003, Journal of the American medical Informatics Association, vol. 10, No. 1, pp. 39-51.

Non-Final Office Action dated Aug. 28, 2007 in U.S. Appl. No. 11/179,384.

Jan. 17, 2008 Response to Non-Final Office Action dated Aug. 28, 2007 in U.S. Appl. No. 11/179,384.

Final Office Action dated Jun. 26, 2008 in U.S. Appl. No. 11/179,384.

Non-Final Office Action dated Jul. 27, 2009 in U.S. Appl. No. 11/265,978.

Non-Final Office Action dated Aug. 24, 2009 in U.S. Appl. No. 11/268,262.

Non-Final Office Action dated May 13, 2009, in U.S. Appl. No. 11/265,979.

Non-Final Office Action dated Dec. 29, 2008 in U.S. Appl. No. 11/179,384.

Final Office Action dated Jul. 24, 2009, in U.S. Appl. No. 11/179,384.

Final Office Action dated Dec. 22, 2009 in U.S. Appl. No. 11/265,979.

Notice of Allowance dated Nov. 19, 2009 in U.S. Appl. No. 11/265,978.

Notice of Allowance, dated Nov. 3, 2009 in U.S. Appl. No. 11/179,384.
Non-Final Office Action dated Apr. 14, 2010 in U.S. Appl. No. 11/944,027.
Non-Final Office Action dated Apr. 16, 2010 in U.S. Appl. No. 11/268,262.
Notice of Allowance, dated Apr. 19, 2010 in U.S. Appl. No. 11/265,978.
Supplemental Notice of Allowance dated May 3, 2010 in U.S. Appl. No. 11/265,978.
Non-Final Office Action dated Aug. 18, 2010 in U.S. Appl. No. 12/702,976.
Non-Final Office Action dated Jul. 8, 2010 in U.S. Appl. No. 11/265,979.
Interview Summary dated Mar. 4, 2010 in U.S. Appl. No. 11/265,979.
Interview Summary dated Nov. 24, 2009 in U.S. Appl. No. 11/268,262.
Interview Summary dated May 12, 2010 in U.S. Appl. No. 11/268,262.
Final Office Action dated Oct. 28, 2010 in U.S. Appl. No. 11/268,262.
Supplemental Notice of Allowance dated Aug. 3, 2010 in U.S. Appl. No. 11/265,978.
Non-Final Office Action dated May 26, 2010 in U.S. Appl. No. 11/942,673.
Interview Summary dated Jul. 26, 2010 in U.S. Appl. No. 11/942,673.
NonFinal Office Action dated Sep. 16, 2010 in U.S. Appl. No. 11/942,687.
Interview Summary dated May 13, 2010 in U.S. Appl. No. 11/944,027.
Non-Final Office Action dated Sep. 29, 2010 in U.S. Appl. No. 11/944,000.
Interview Summary dated Dec. 1, 2010, 2010 in U.S. Appl. No. 12/702,976.
Interview Summary dated Nov. 16, 2010 in U.S. Appl. No. 11/265,979.
Interview Summary dated Dec. 1, 2010 in U.S. Appl. No. 11/268,262.
Notice of Allowance dated Dec. 1, 2010 in U.S. Appl. No. 11/268,262.
Final Office Action dated Nov. 26, 2010 in U.S. Appl. No. 11/942,673.
Interview Summary dated Dec. 3, 2010 in U.S. Appl. No. 11/942,687.

* cited by examiner

SYSTEMS AND METHODS FOR INTERLEAVING SERIES OF MEDICAL IMAGES

CROSS-REFERENCE TO RELATED APPLICATIONS

This application claims priority under 35 U.S.C. §119(e) to U.S. Provisional Application Ser. No. 60/625,690, filed on Nov. 4, 2004, which is hereby expressly incorporated by reference in its entirety.

BACKGROUND OF THE INVENTION

1. Field of the Invention

This invention relates to management and viewing of medical images and, more particularly, to systems and methods of comparing related medical images in order to detect differences in the compared images.

2. Description of the Related Art

Medical imaging is increasingly moving into the digital realm. This includes imaging techniques that were traditionally analog, such as mammography, x-ray imaging, angiography, endoscopy, and pathology, where information can now be acquired directly using digital sensors, or by digitizing information that was acquired in analog form. In addition, many imaging modalities are inherently digital, such as MRI, CT, nuclear medicine, and ultrasound. Increasingly these digital images are viewed, manipulated, and interpreted using computers and related computer equipment. Accordingly, there is a need for improved systems and methods of viewing and manipulating these digital images.

When comparison of related images is required, subtle differences between images may be difficult to detect. For example, if a lung radiograph from two months previous, and a current lung radiograph are to be compared in order to determine if any changes have occurred in the lungs over the previous two months, the viewer or reader typically views the two x-rays side by side. For example, the viewer or reader may have two monitors placed side by side, wherein each of the monitors displays a chest radiographic image. Alternatively, the viewer may view the two images side by side on a single monitor. However, as those of skill in the art will recognize, identifying differences in related images in this manner is often tedious and difficult. Some imaging modalities, such as CT and MRI, produce a large number of images, hundreds to even thousands of images per exam. In many cases, comparison of different series of images within the exam is required. For example, comparison of pre and post contrast images to detect areas of enhancement or comparison of PET and CT images for localization of activity is often necessary. Further, these often large exams may need to be compared to multiple prior exams to detect subtle, progressive changes over time, for example to detect a small, growing tumor. Current imaging software does not provide a satisfactory method for comparing images contained in two or more image series. Accordingly, systems and methods for comparison of images of multiple image series so that differences in the images may be more easily distinguishable are desired.

SUMMARY OF THE INVENTION

In one embodiment, a method of viewing medical images from two or more image series on a display device coupled to a computing device comprises the steps of selecting a first image series comprising two or more medical images, selecting at least one comparison image series, each of the comparison image series comprising two or more medical images, interleaving images of the first image series and the comparison image series in order to form an interleaved image series, and sequentially displaying the images of the interleaved image series at a single location on the display device.

In another embodiment, a method of viewing a series of medical images on a display device coupled to a computing device comprises the steps of (a) selecting a first image series for viewing, the first image series comprising a plurality X of medical images, (b) selecting a second image series for viewing, the second image series comprising a plurality Y of medical images, (c) displaying at a predetermined location on the display device a Nth image of the first image series, (d) replacing the Nth image of the first image series with a Mth image of the second image series at the predetermined location, (e) incrementing N and M, and (f) repeating steps (c) to (f).

In another embodiment, a system for enhancing a viewer's ability to detect differences between medical images in two or more sets of medial images comprises a display device, a graphical user interface displayed on the display device and comprising an image pane configured to display a single medical image at a time, an image selection module to select two or more sets of medical images, each of the sets of medical images comprising two or more medical images, and a user interface to receive commands from a user, wherein in response to receiving a first command from the user, the image pane sequentially displays a first medical image from each of the image sets and, after displaying the first medical image from each image set, the image pane sequentially displays a second medical image from each image set. This process of displaying images from images series alternatively continues through subsequent images in the image series.

In another embodiment, a system of viewing medical images from two or more image series on a display device coupled to a computing device comprises means for selecting a first image series comprising two or more medical images, means for selecting at least one comparison image series, each of the comparison image series comprising two or more medical images, means for interleaving images of the first image series and the comparison image series in order to form an interleaved image series, and means for sequentially displaying the images of the interleaved image series at a single location on the display device.

In another embodiment, a method of forming an interleaved image series comprises selecting N groups of images, each of the groups of images comprising two or more images, determining a starting image of each of the groups of images, creating an interleaved image series comprising images from each of the selected N groups of images, wherein the images of the interleaved image series are ordered so that an image from each of the N groups of images is included in each sequential Nth group of images, and providing the interleaved image series to a user interface for sequential display in a predetermined location of a display device.

DETAILED DESCRIPTION OF EMBODIMENTS OF THE INVENTION

Embodiments of the invention will now be described with reference to the accompanying figures, wherein like numerals refer to like elements throughout. The terminology used in the description presented herein is not intended to be interpreted in any limited or restrictive manner, simply because it is being utilized in conjunction with a detailed description of certain specific embodiments of the invention. Furthermore, embodiments of the invention may include several novel features, no single one of which is solely responsible for its desirable attributes or which is essential to practicing the inventions herein described.

Figure 1:
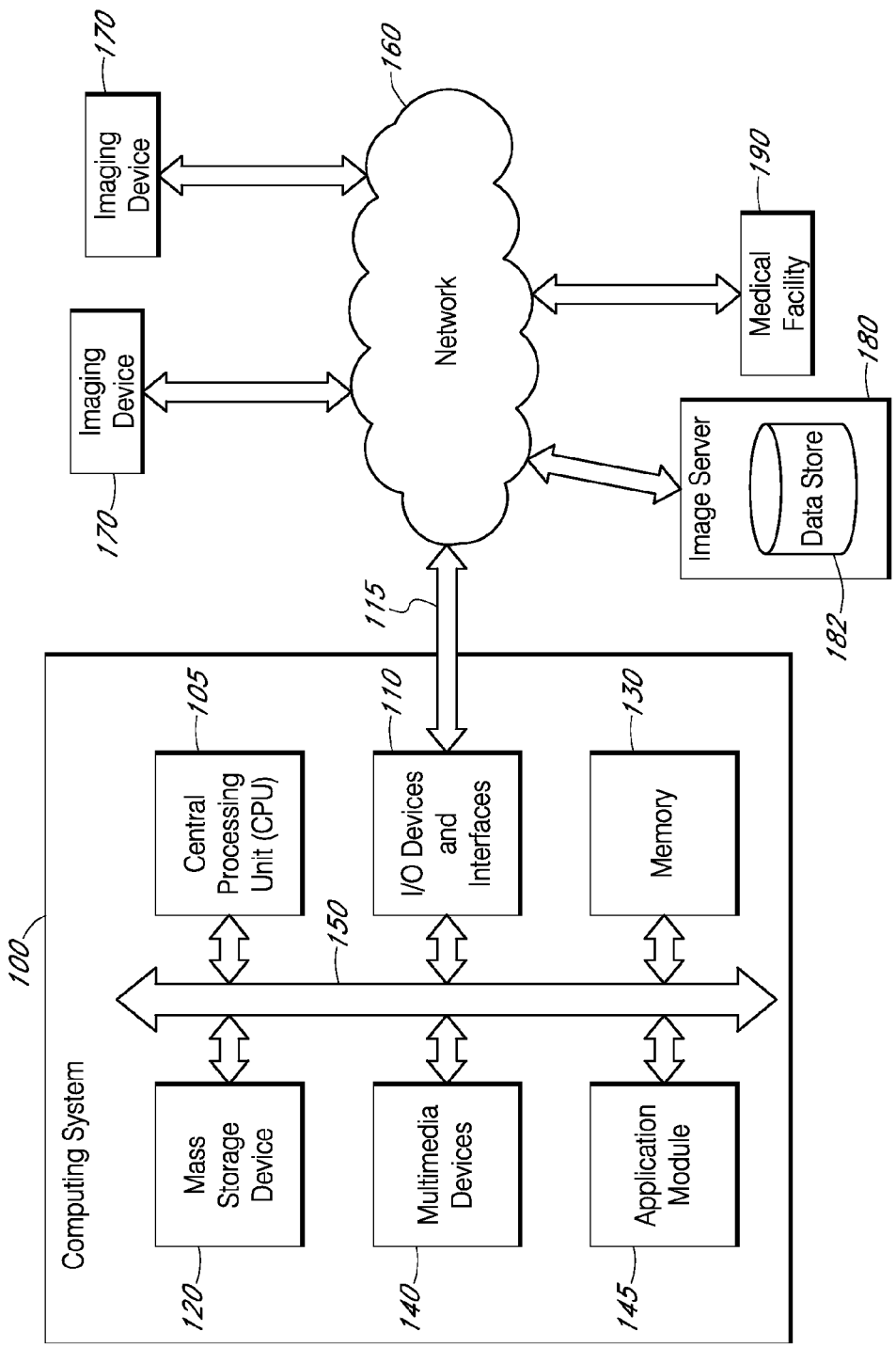
FIG. 1 is a block diagram of an exemplary computing system in communication with a network and various networked devices.

FIG. 1 is a block diagram of an exemplary computing system 100 in communication with a network 160 and various network devices. The computing system 100 may be used to implement certain systems and methods described herein. The functionality provided for in the components and modules of computing system 100 may be combined into fewer components and modules or further separated into additional components and modules.

The computing system 100 includes, for example, a personal computer that is IBM, Macintosh, or Linux/Unix compatible. In one embodiment, the exemplary computing system 100 includes a central processing unit ("CPU") 105, which may include a conventional microprocessor, an application module 145 that comprises one or more various applications that may be executed by the CPU 105. The application module 145 may include, by way of example, components, such as software components, object-oriented software components, class components and task components, processes, functions, attributes, procedures, subroutines, segments of program code, drivers, firmware, microcode, circuitry, data, databases, data structures, tables, arrays, and variables.

The computing system 100 further includes a memory 130, such as random access memory ("RAM") for temporary storage of information and a read only memory ("ROM") for permanent storage of information, and a mass storage device 120, such as a hard drive, diskette, or optical media storage device. Typically, the modules of the computing system 100 are connected to the computer using a standards-based bus system. In different embodiments of the present invention, the standards based bus system could be Peripheral Component Interconnect (PCI), Microchannel, SCSI, Industrial Standard Architecture (ISA) and Extended ISA (EISA) architectures, for example.

The computing system 100 is generally controlled and coordinated by operating system software, such as the Windows 95, 98, NT, 2000, XP or other compatible operating systems. In Macintosh systems, the operating system may be any available operating system, such as MAC OS X. In other embodiments, the computing system 100 may be controlled by a proprietary operating system. Conventional operating systems control and schedule computer processes for execution, perform memory management, provide file system, networking, and I/O services, and provide a user interface, such as a graphical user interface ("GUI"), among other things.

The exemplary computing system 100 includes one or more of commonly available input/output (I/O) devices and interfaces 110, such as a keyboard, mouse, touchpad, and printer. In one embodiment, the I/O devices and interfaces 110 include one or more display devices, such as a monitor, that allows the visual presentation of data to a user. More particularly, display devices provide for the presentation of GUIs, application software data, and multimedia presentations, for example. In one embodiment, a GUI includes one or more image panes in which medical images may be displayed. As described in further detail below, a GUI may provide a comparison pane on a display device in which images from multiple image series are sequentially displayed. According to the systems and methods described below, medical images may be stored on the computing system 100 or another device that is local or remote, displayed on a display device, and manipulated by the application module 145. The computing system 100 may also include one or more multimedia devices 140, such as speakers, video cards, graphics accelerators, and microphones, for example.

In the embodiment of FIG. 1, the I/O devices and interfaces 110 provide a communication interface to various external devices. In the embodiment of FIG. 1, the computing system 100 is coupled to a network 160, such as a LAN, WAN, or the Internet, for example, via a communication link 115. The network 160 may be coupled to various computing devices and/or other electronic devices. In the exemplary embodiment of FIG. 1, the network 160 is coupled to imaging devices 170, an image server 180, and a medical facility 190. In addition to the devices that are illustrated in FIG. 1, the network 160 may communicate with other computing, imaging, and storage devices.

The imaging devices 170 may be any type of device that is capable of acquiring medical images, such as a MRI, x-ray, mammography, or CT scan systems. The image server 180 includes a data store 182 that is configured to store images and data associated with images. In one embodiment, the imaging devices 170 communicate with the image server via the network 160 and image information is transmitted to the image server 160 and stored in the data store 182. In one embodiment, the image data is stored in Digital Imaging and Communications in Medicine ("DICOM") format. The complete DICOM specifications may be found on the National Electrical Manufactures Association Website at <medical.nema.org>. Also, *NEMA PS 3—Digital Imaging and Communications in Medicine,* 2004 ed., Global Engineering Documents, Englewood Co., 2004, provides an overview of the DICOM standard. Each of the above-cited references is hereby incorporated by reference in their entireties. In one embodiment, the data store 182 also stores the user-defined display parameters associated with one or more of the images stored on the data store 182. As discussed in further detail below, the user-defined display parameters may vary depending of the type of image, area imaged, clinical indication, source of image, display device, user, or other factors. Accordingly, any type of user-defined display parameter is expressly contemplated for use in conjunction with the systems and methods described herein.

The exemplary image server 180 is configured to store images from multiple sources and in multiple formats. For example, the image server 180 may be configured to receive medical images in the DICOM format from multiple sources, store these images in the data store 182, and selectively transmit medical images to requesting computing devices.

The medical facility 190 may be a hospital, clinic, doctor's office, or any other medical facility. The medical facility 190 may include one or more imaging devices and may share medical images with the image server 180 or other authorized computing devices. In one embodiment, multiple computing systems, such as the computing system 100 may be housed at a medical facility, such as medical facility 190.

DEFINITION OF TERMS

"Medical image" is defined to include an image of an organism. It may include but is not limited to a radiograph, computed tomography (CT), magnetic resonance imaging (MRI), Ultrasound (US), mammogram, positron emission tomography scan (PET), nuclear scan (NM), pathology, endoscopy, ophthalmology, or many other types of medical images. While this description is directed to viewing and tracking of medical images, the methods and systems described herein may also be used in conjunction with non-medical images, such as, images of circuit boards, airplane wings, and satellite images, for example.

"Modality" is defined as a medical imaging device (a patient who undergoes an MRI is said to have been scanned with the MRI modality).

"Image series" refers to two or more images that are related. For example, an image series may comprise two or more images of a particular patient that are acquired on a particular date, e.g., different x-ray projections of the chest. A series of contiguous 3 mm axial CT scans of the chest would be another example of an image series. A brain MRI scan might include the following series: sagittal T1 weighted images, axial T1 weighted images, axial FLAIR images, axial T2 weighted images, as well as post contrast axial, sagittal and coronal T1 weighted series. An image series may be limited to images of a certain modality or may comprise images of multiple modalities.

"Patient" refers to an individual who undergoes a medical imaging examination.

"Display parameters" are defined to include methods of display of an image or exam. Display parameters may include, for example, a pixel window level and width (similar to brightness and contrast), a certain color map that renders different pixel intensities as different colors, or opacity map.

"Interleaving," is defined to include the process of arranging images from multiple image series by regularly alternating between images of the multiple image series in order to create a resultant "interleaved" image series. In one embodiment, an interleaved image series comprises images from multiple image series ordered so that the interleaved image series alternates between the images of the original series. For example, when image series A comprising images A1, A2, . . . An, image series B comprising images B1, B2, . . . Bn, and image series C comprising images C1, C2, . . . Cn are interleaved, the resultant interleaved image series is ordered: A1, B1, C1, A2, B2, C2, . . . An, Bn, Cn. Images from multiple image series may be interleaved in various patterns and multiple interleaved image series may be generated from two or more image series.

Figure 2:
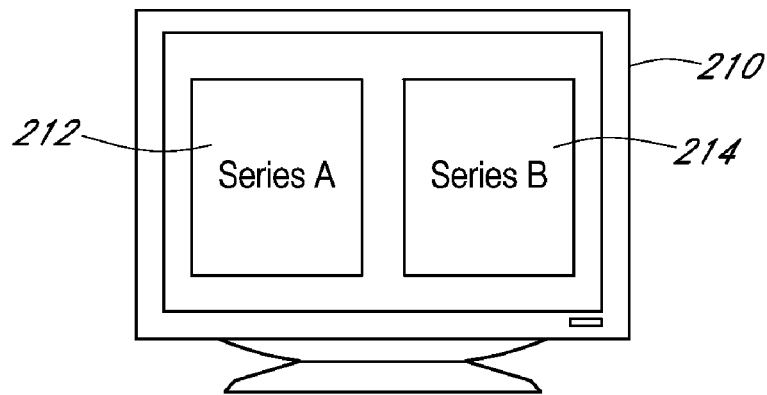
FIG. 2 is a diagram illustrating a display device having images from two image series concurrently displayed in image panes displayed on a display device.

FIG. 2 is a diagram illustrating a display device having images from two image series concurrently displayed in image panes 212, 214 displayed on a display device 210. In the discussion that follows, the display device 210 is coupled to a computing device, such as computing device 100, and receives display information from the computing device 100. While the systems and methods described below for interleaving and viewing images of multiple image series may be controlled by any suitable computing device, for ease of explanation herein, reference will be made to a display device coupled to computing device 100.

In the embodiment of FIG. 2, an image of a series A image series is displayed in the image pane 212, while an image of the series B image series is displayed in the image pane 214. As noted above, each image series comprises a group of images that are related in some way, such as having been acquired from a patient on a particular day. Although only a single image of each of the image series is simultaneously displayed on the display device 210, the series A and series B image series each comprise multiple images.

In certain embodiments, such as where the series A and B images are related, e.g., series A comprises mammogram images of a patient taken on a first date and series B comprises the mammogram images of the same patient taking on a later date, it may be advantageous to identify differences between the images of Series A and Series B. However, as described above, it is difficult to distinguish minor or small differences between images using currently available image comparison techniques. Using current image comparison systems, if a lung radiograph from two months previous, and a current lung radiograph are to be compared in order to determine if any changes have occurred in the lungs over the previous two months, the viewer or reader typically views the two x-rays side by side, such as in image panes 212, 214 illustrated in FIG. 2. As those of skill in the art will recognize, identifying differences in related images in this manner is often tedious and difficult. Accordingly, described hereinafter are exemplary systems and methods for comparison of images of multiple image series so that differences between (in contrast to within) the images may be more easily distinguishable. In certain embodiments, related images are displayed sequentially in a single viewing pane on a display device so that difference between the images may be more easily detected. The systems and methods described herein are applicable to any two or more images, including multiple images of multiple image series, for example.

Figure 3:
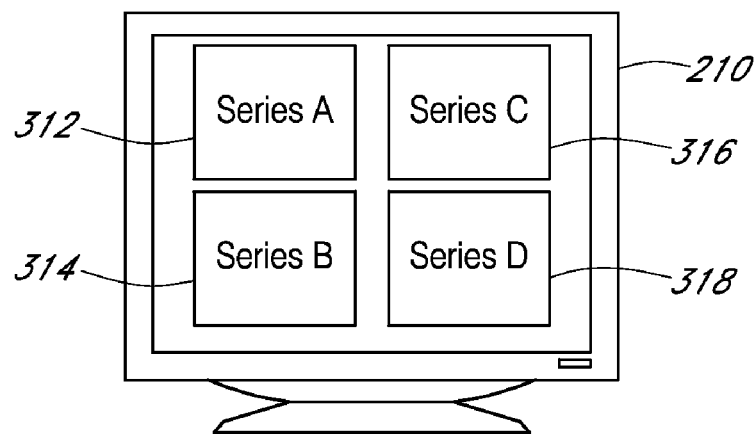
FIG. 3 is a diagram illustrating a display device having images from four image series concurrently displayed in image panes.

FIG. 3 is a diagram illustrating a display device having images from four image series concurrently displayed in image panes 312, 314, 316, in 318. In the embodiment of FIG. 3, the image pane 312 displays images from series A, the image pane 314 displays images from series B, the image pane 316 displays images from series C, and the image pane 318 displays images from series D. Thus, a single image from each of the four image series A-D is concurrently displayed on the display device 210. In certain prior art systems, comparison of images of multiple series was performed using a graphical user interface such as displayed in FIG. 3, wherein the user distinguishes differences between images that are displayed side-by-side on a display device.

Figure 4:
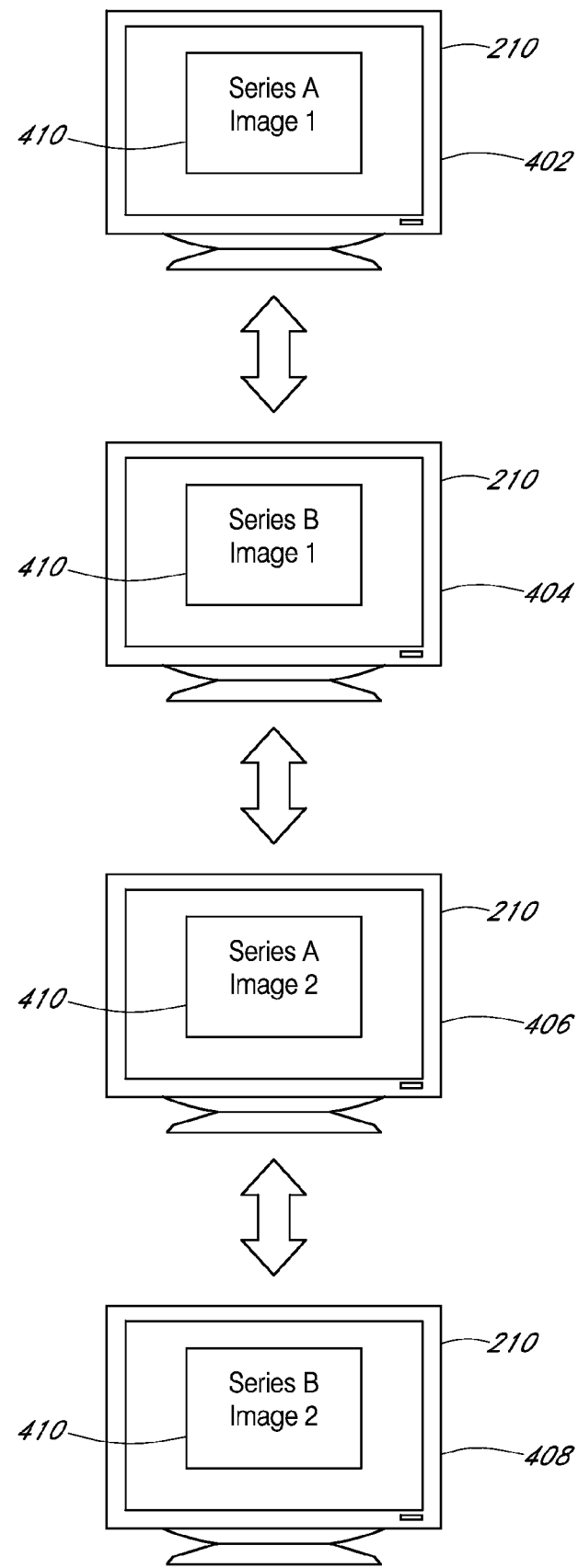
FIG. 4 is a diagram illustrating sequential changes to a comparison pane displayed on the display device as images from two image series are compared.

FIG. 4 is a diagram illustrating sequential changes to a comparison pane 410 displayed on the display device 210 as images from two image series are compared. The comparison pane 410 is configured to display a single image. In one embodiment, one of the display panes, e.g. display pane 312 on display device 210, serve as the comparison pane 410. In the embodiment of FIG. 4, images from two image series, images series A and B, have been selected for comparison. After being selected for comparison using any suitable selection method, images from series A and B are interleaved so that they are alternatively displayed in the comparison pane 410.

In embodiments with more than two series, the interleaved images may be ordered according to various schemes. For example images from four image series may be ordered as follows: first image of first image series, first image of second image series, first image of third image series, first image of fourth image series, second image of first image series, and so forth. In other embodiments, however, the interleaved images may be ordered differently. For example, images from four image series may also be ordered as follows: first image of first image series; first image of second image series; first image of first image series; first image of third image series; first image of first image series; and first image of fourth image series. Any other ordering of images from multiple image series falls within the scope of "interleaving" as used herein.

FIG. 4 shows the display device 210 at four steps 402, 404, 406, 408 of the comparison process, where the comparison process describes the process of displaying images in an interleaved image series. More particularly, in step 402, a first image of image series A is displayed in the comparison pane 410. Moving to step 404, the first image of image series A is replaced by a first image of image series B in the comparison pane 410. Assuming the images of series A and B are of the same subject, the image displayed in steps 402 and 404 may be very similar. Accordingly, if differences exist in the first images of series A and B, these differences may be more easily detectable as the display device cycles between the two images. Comparison of images in an interleaved image series may be more advantageous if the images of each selected image series are of a common anatomical area, common image size, common image orientation, and the images are in the same order.

In one embodiment, the computing system 100 that is coupled to the display 210 may store settings for displaying images of particular image series, such as, for example, time for displaying each image, resolution of each image, cropping to be applied to each image, and any other setting that maybe appropriate. In one embodiment, the time for displaying an image may be determined real time by the user. For example, the user may press a designated key on a keyboard or mouse in order to indicate that the current image should be replaced with an adjacent image in the interleaved image series. In another embodiment, the user selects settings for display of the images. For example, the user may select an appropriate zoom level of an image series that should be applied to each image in the image series.

Thus, the images of series A may be magnified more or less than the images of series B. In addition, the user may adjust any other visualization settings for individual images, an entire image series, or two or more image series.

With the first image of series B displayed in the comparison pane 410 (step 404), the user may initiate viewing of an adjacent image in the interleaved image series by pressing a certain key on a keyboard or mouse, for example. In one embodiment, a first input from a mouse indicates that a next image, e.g. image 2 of series A (step 406) should be displayed in the comparison pane 410 and a second input from the mouse indicates that a previous image, e.g. image 1 of series A (step 402) should again be displayed in the comparison pane 410. In one embodiment, the first input is entered by the user moving a scroll button on the mouse in a first direction and the second input is entered by the user moving the scroll button on the mouse in an opposite direction. Thus, the user may change the content of the comparison pane 410 to either a next or a previous image in the interleaved image series. For example, at step 404, if the user wishes to again view the first image of series A, e.g., in order to locate difference in the first images of series A and B, the user may provide an input to the computing device 100 indicating movement to a previous image. Alternatively, at step 404, if the user wishes to view a next image in the interleaved image series, the user may provide an input to the computing device 100 indicating movement to a next image.

At step 406, the second image of series A is displayed in the comparison pane 410, replacing the first image of series B (step 404). At step 406, the user may provide inputs to the computing device 100 indicating that the comparison pane 410 should be updated with a previous image, e.g. step 404, or a subsequent image, e.g., step 408.

At step 408, the second image of series B is displayed in the comparison pane 410, replacing the second image of series B (step 406). At step 406, the user may provide inputs to the computing device 100 indicating that the comparison pane 410 should be updated with a previous image, e.g. step 404, or a subsequent image. In one embodiment, each of the image series A and B include more than two images, such as 3 or more images, and the images of series A and B are displayed in the manner described above with respect to FIG. 4. In one embodiment, more than two images series may be interleaved for display in the comparison pane. For example, if three images series, e.g., series A, B, and C, are selected for comparison, a first image of each of the series will be sequentially displayed in the comparison pane, followed by a second image of each of the series, and so on. As noted above, the user may control the timing of transition between display of images in the interleaved image series and may even control the direction of movement in the interleaved series. Additionally, the user may control alignment and/or positioning of the images of each images series in order to precisely align interleaved images from multiple series.

In one embodiment, the images of each of the image series are automatically modified so that characteristics of the images are similar. For example, images may be adjusted by changing their size, rotation, and location. If the images are of substantially the same anatomical structure, when the images of the interleaved image series are displayed in the comparison pane, differences between adjacent images may be more easily detected. In one embodiment, selected images are morphed in order to achieve a common size of the anatomical structure of interest in each of the images. In one embodiment, photographic filters may be applied to all images of one or more image series, or to selected images of one or more image series, to further enhance the viewer's ability to distinguish differences in the images.

In one embodiment, information regarding the image currently displayed in the comparison pane 410 is displayed on the display device 210 and updated as the images in the comparison pane 410 are changed. For example, information regarding the images series and image number within the series may be displayed for each image. In addition, the exam date and time may also be displayed and updated as the images of the interleaved image series are displayed in the comparison pane 410. In one embodiment, an indicator of whether the current display is of an interleaved image series or a single image series is displayed on the display device. For example, "interleaved" may be displayed at the top of the display device when an interleaved image series is displayed in a comparison pane. In some embodiment, the user chooses what information related to the images of the interleaved image series should be displayed. The user may also be provided the ability to turn the display of information on and off, such as by pressing a particular key or key combination on the keyboard.

Figure 5:
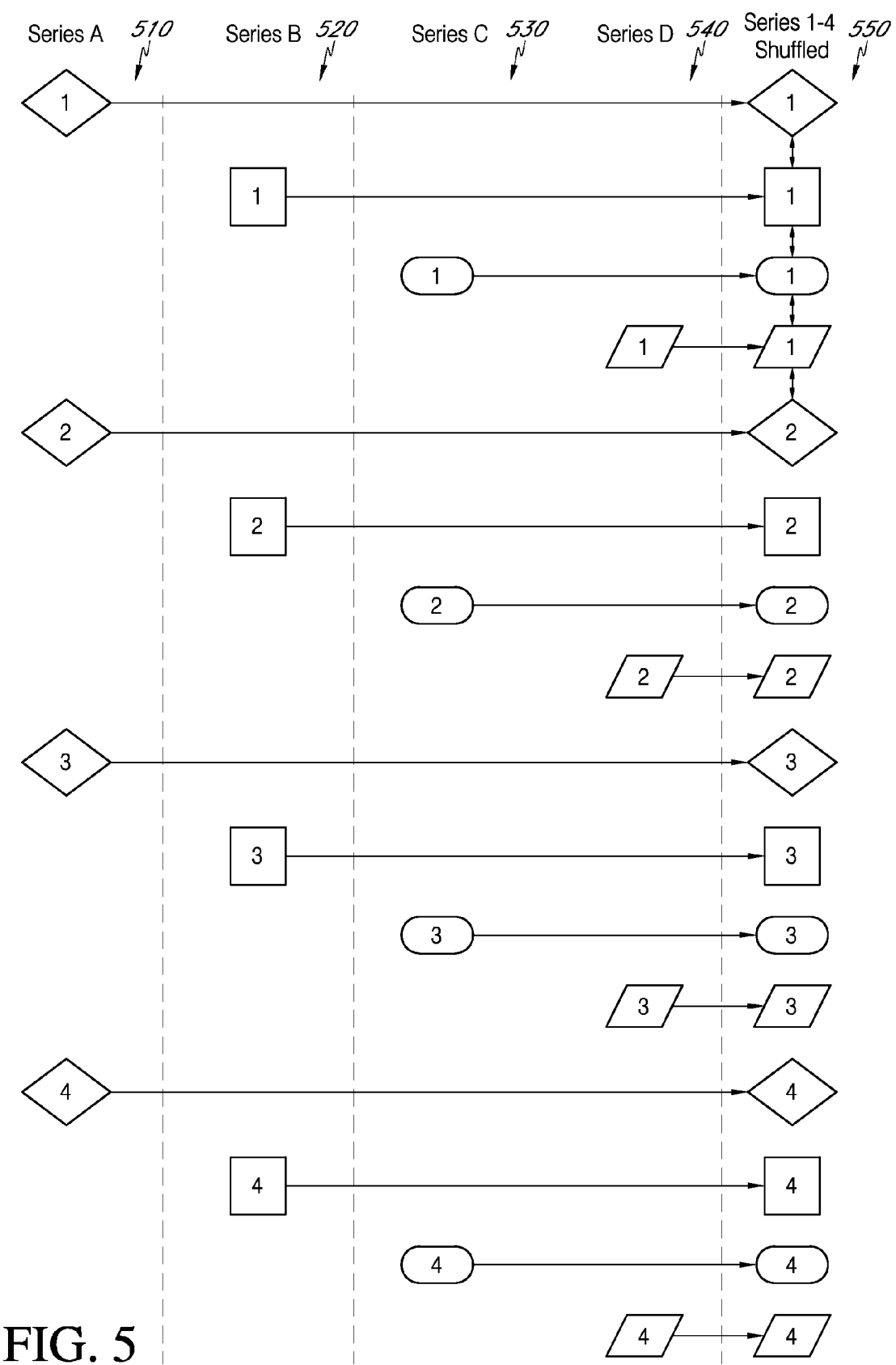
FIG. 5 is a diagram illustrating an exemplary interleaving of four image series.

FIG. 5 is a diagram illustrating an exemplary interleaving of four image series in creating an interleaved image series. As noted above, the image series that are selected for comparison, and thus, are selected for interleaving, may be selected by a user in one of several manners or may be automatically selected by the computing device based on properties of the image series. In one embodiment, the multiple image series are interleaved so that a first image of each series is displayed in the comparison pane prior to display of a second image of any of the other selected image series. FIG. 5 illustrates an exemplary interleaving of four image series, series A, B, C, and D, each comprising four images. As those of skill in the art will recognize, more or less image series, each comprising more or less images, may be interleaved in a manner similar to that illustrated in FIG. 5.

In FIG. 5, the images of series A are represented by diamonds in a column 510, where a number in each of the diamonds represents a specific image within image series A. Similarly, images of series B are represented by squares in column 520, series C are represented by ovals in a column 530, and series D are represented by parallelograms in a column 540. Each of the images in images series B, C, and D are likewise numbered 1-4, indicating a particular image in each image series. As noted above, the first image selected for comparison in a particular image series may not be the first image in the image series, e.g., the first image of an exam. Thus, although each image series A-D begins with a first image labeled image "1", this first image may not be the first image in the image series, but may be a user selected, or automatically selected, start image. In addition, each of the images may have user-defined display parameters that are different than other images of the same series and/or other image series. In some embodiments, display parameters, such as zoom level, cropping, and color characteristics, may be simultaneously changed for each image in an image series, such as series A, B, C, D, or an interleaved image series, such as interleaved image series 540.

As illustrated in FIG. 5, an interleaved image series 550 each of the images 1-4 in each of the image series A-D. More particularly, the interleaved image series 550 comprises a first image from each of series A-D, followed by a second image from each of the series A-D, followed by a third image from each of the series A-D, followed by a fourth image from each of the series A-D. Thus, when the interleaved image series 550 is displayed in the comparison pane, a first image of the image series A is displayed, followed by a first image of image series B, a first image of image series C, and a first image of image series D. While the order of the interleaved image series 550 is maintained during viewing of the interleaved images, the direction of movement between adjacent images may be selected by the user or automatically by the computing device 100.

Figure 6:
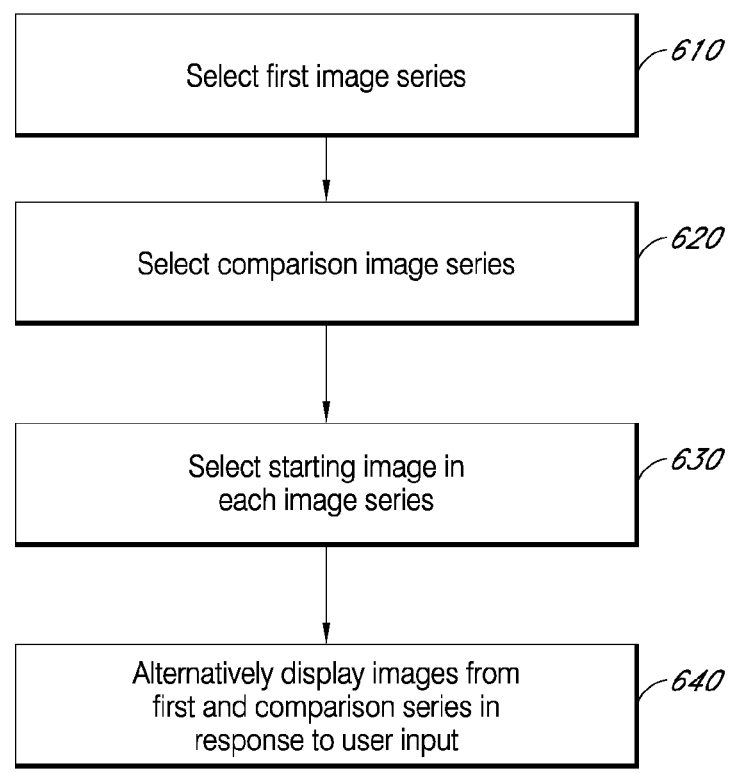
FIG. 6 is a flowchart illustrating an exemplary method of viewing images from multiple image series.

FIG. 6 is a flowchart illustrating an exemplary method of viewing images from multiple image series. Using the method of FIG. 6, multiple image series may be easily compared and differences between images of the multiple image series may be distinguished.

In a block 610, a first image series is selected. As noted above, an image series is a group of two or more images that are in some way related. For example, a first image series may comprise multiple chest x-rays of a patient that are taken on a given date.

In a block 620, one or more comparison image series are selected. These image series also each comprise two or more images that are in some way related, such as having been taken at a common exam. The comparison image series should be related to the first image series so that when the first image series and the comparison image series are compared, meaningful distinctions between the image series may be detected.

In one embodiment, the first image series and the comparison image series are selected by the user clicking on a button indicating that image interleaving is desired. In one embodiment, a user right-clicks with a mouse on an image of a first image series in order to initiate display of an "interleave menu" listing options for selecting image series for interleaving and viewing the interleaved image series. In one embodiment, the interleave menu includes an option, such as "interleave adjacent," indicating that the user may select one of the other image series displayed on the display for interleaving. In certain embodiments, any number of image panes may be simultaneously displayed on the display device 210. For example, in FIG. 2, two image panes 212, 214 are display and in FIG. 3, four image panes 312, 314, 316, 318 are displayed. In other embodiment, six, eight, ten, twelve, or more image panes may be concurrently displayed on the display device.

When the interleave adjacent option is selected, the user may select one or more comparison series by moving the pointer to a border between the adjacent series and clicking the mouse button. In one embodiment, the cursor icon changes when it is positioned in a border indicating that the adjacent image series may be selected for comparison by clicking the mouse button. With reference to FIG. 3, for example, the user may right click on the image pane 314 in order to select series B as the first image series and to initiate display of the interleave menu. From the interleave menu, if the user selects interleave adjacent, the user may then move the pointer to the border between the image panes 312 and 314 and click the mouse button in order to select series A as a comparison image series. In one embodiment, selecting a comparison image series initiates creation of an interleaved image series and displays the first image of the interleaved image series in the comparison pane. In an embodiment when only two image series are represented on the display device, such as FIG. 2, selection of interleave adjacent from the interleave menu may automatically select the two displayed image series for interleaving and initiate creation and viewing of a interleaved image series.

In one embodiment, the interleave menu also includes an option that allows the user to select an adjacent image series for interleaving and, after selection of the first and comparison image series, displays images of the interleaved images series in a comparison pane that covers the entire display area, or substantially all of the display area, of the display device. In this way, the images of the selected image series may be viewed at a higher magnification level and, accordingly, differences in the images may be more easily detectable. Thus, in an embodiment that displays four image panes on the display device (e.g., FIG. 3), after selection of this option from the interleave menu, a single click on a comparison image series may cause the computing device to generate an interleaved image series and display a first image of the interleaved image series in a comparison pane that covers substantially all of the display area of the display device, e.g., the area previously covered by the four image panes 312, 314, 316, 318 or FIG. 3. Advantageously, this "interleave and jump to full screen display" option on the interleave menu provides an efficient transition from display of many image series to the display of a single interleaved series in a comparison pane that covers all, or substantially all, of the display area of a display device.

In one embodiment, the interleave menu includes an option that initiates automatic selection of one or more comparison image series based upon characteristics of the selected first image series. For example, image series with the same or similar names may be selected as comparison image series. In addition, image series may be selected automatically based upon any other criteria, such as one or more information items contained in the DICOM headers of images. In one embodiment, when this option is chosen from the interleave menu, a list of image series that have the same series name, or other criteria that may be user defined, may be displayed. The user may then select one or more of the displayed series as comparison image series.

The interleave menu advantageously allows the user to select image series for interleaving and automatically display the generated interleaved image series with minimal input from the user. For example, after selecting "interleave adjacent" on the interleave menu, a single click of a mouse, for example, on a border between the images to be interleaved causes the computing system 100 to generate an interleaved image series and display a first image of the interleaved image series in a comparison pane on the display device.

Returning to the diagram of FIG. 6, in a block 630, a starting image of each of the image series is selected. In one embodiment, a first image of the first image series and each of the comparison image series are displayed on a display device. A user, using an input device, such as a mouse or keyboard, may cycle through the images in each of the image series in order to determine a first image for comparison. For example, images of certain modalities, such as CT and MRI images, may not have starting images that are each taken at similar physical locations within the patient. Thus, in these embodiments the user may select a different starting image in each of the image series so that adjacent images in the interleaved image series are more closely related. For example, if the images series to be interleaved are series A comprising images A1, A2, . . . An, series B comprising images B1, B2, . . . Bn, and series C comprising images C1, C2, . . . Cn, the user may select images A1, B3, and C5 as the starting images of the respective image series so that the resultant interleaved image series is ordered A1, B3, C5, A2, B4, C6, A3, B5, C7, . . . Ax, Bx+2,Cx+4.

In an advantageous embodiment, the starting image in each of the series should be related so that meaningful differences between the images of the image series are detectable. In one embodiment, the user may adjust display characteristics of each image in an image series by adjusting the display characteristics of the image currently displayed from the desired image series. For example, if the first image series is at a higher zoom level than the comparison image series, the zoom level of each image in the first image series may be adjusted by adjusting the zoom level of the currently display image of the first image series.

After selecting the first image series and the comparison image series, and selecting the display characteristics of one or more of the images which are then applied to the other images in the series to which it belongs, the image series are interleaved so that an interleaved image series is created, as illustrated in FIG. 5, for example.

In a block 640, images from the interleaved image series are displayed in a comparison pane displayed on the display device. In one embodiment, the comparison pane fills substantially the entire display area of a display device. In another embodiment, the comparison pane is smaller than a total display area of the display device. In one embodiment, a user input determines when a current image displayed in the comparison pane is updated with an adjacent image, by moving a scroll wheel on a mouse while pressing a mouse button, for example. In one embodiment, when the user has completed viewing the interleaved image series, the previous layout on the display device may be restored by the user performing a specific action, such as releasing the mouse button that is depressed while viewing interleaved images.

Figure 7B:
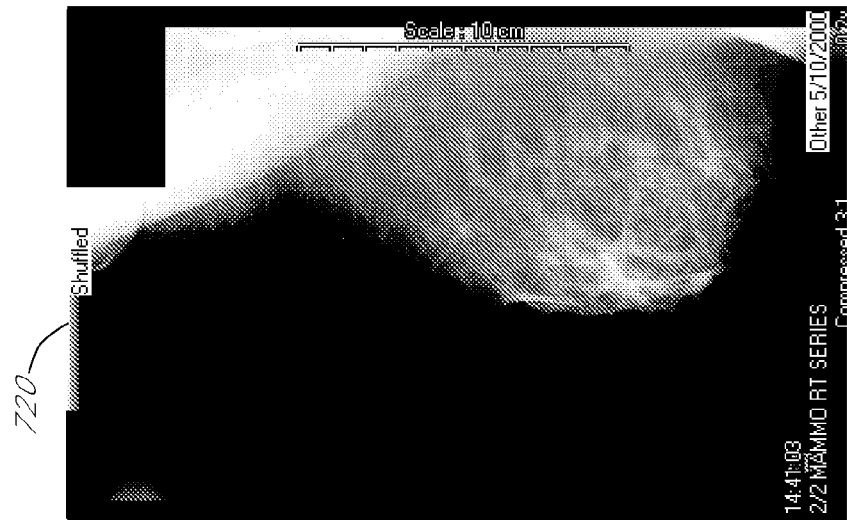
FIGS. 7A and 7B are images of a first image series.
Figure 7A:
Figure 8B:
FIGS. 8A and 8B are images of a second image series.
Figure 8A:
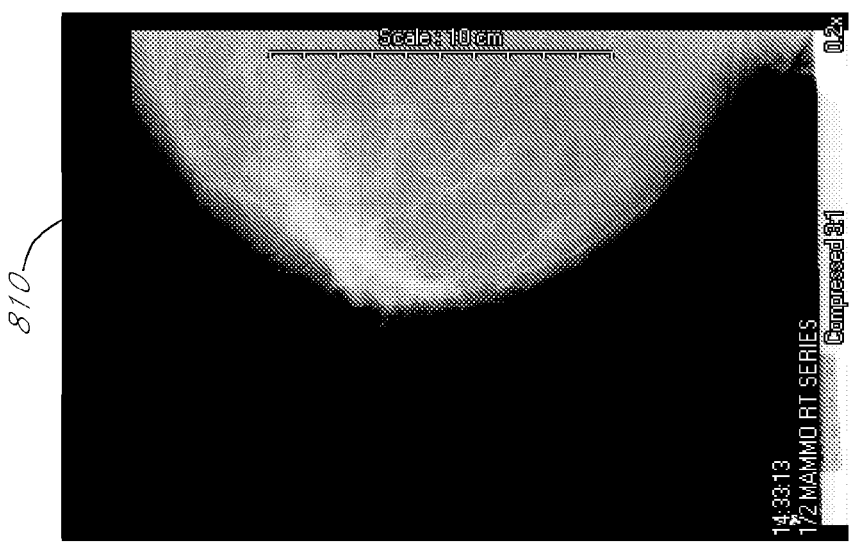
Figures 9A, 9B, 9C, 9D:
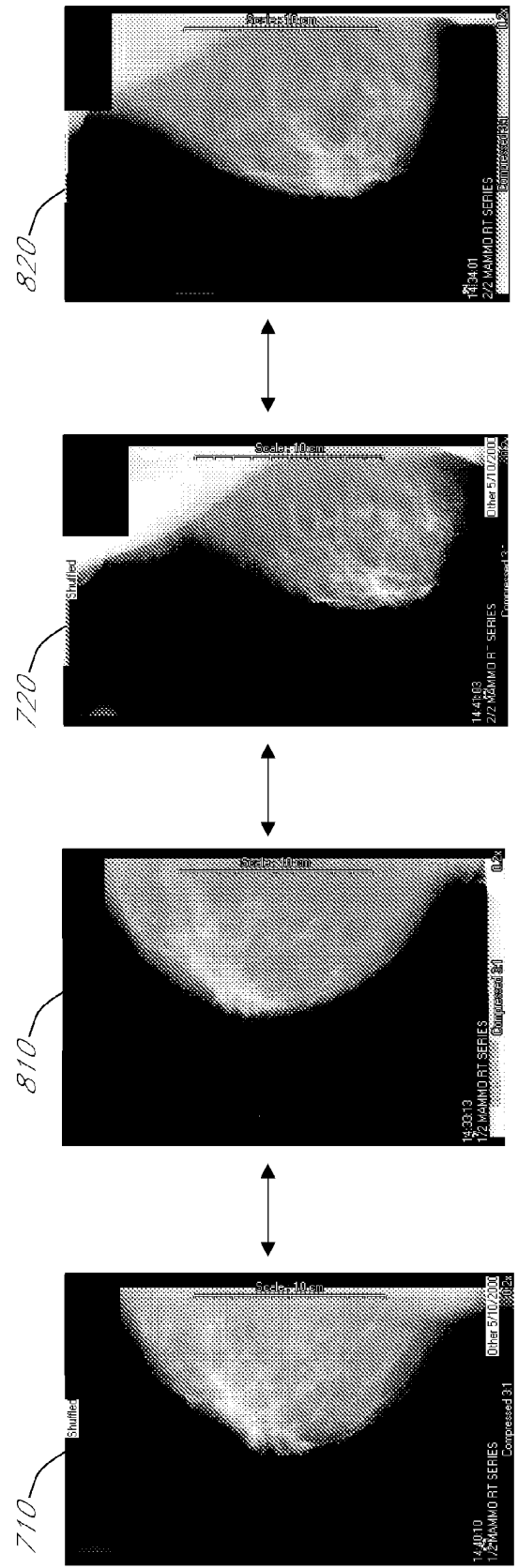
FIGS. 9A-9D are the images of the first and second image series interleaved for sequential viewing in a predetermined portion of a display.

FIGS. 7A and 7B are images of a first image series, FIGS. 8A and 8B are images of a second image series, and FIGS. 9A-9D are the images of an interleaved image series comprising images of the first and second image series. More particularly, FIGS. 7A and 7B are two mammographic images 710, 720 in a first image series. In one embodiment, the images 710, 720 are of a patient on a first date. FIGS. 8A and 8B are two mammographic images 810, 820 in a second image series. In one embodiment, the images 710, 720, 810, 820 are of the same patient, but the images 810, 820 were taken at a later date than the images 710, 720. Thus, differences between the earlier mammographic images 710, 720 and the later mammographic images 810, 820 may be useful in detection and diagnosis of the patient. Accordingly, comparison of the images of the images series illustrated in FIGS. 7 and 8 may allow detection of differences between the earlier and later images.

FIGS. 9A-9D are the images of FIGS. 7 and 8 combined in an interleaved image series for viewing in a comparison pane. For example, image 710 may first be displayed in a comparison pane. When the user indicates that a next image should be displayed, image 810 may replace image 710 in the comparison pane. With image 810 displayed in the comparison pane, when the user indicates that a next image should be displayed, image 720 is replaced with image 810 in the comparison pane. With image 720 displayed in the comparison pane, when the user indicates that a next image should be displayed, image 720 is replaced with image 820 in the comparison pane. As noted above, however, movement between images in an interleaved image series, such as that of FIG. 9, may be bidirectional so that the user may move back and forth between images as desired.

In another embodiment, interleaving of image series produces two or more interleaved image series. In one embodiment, the first image of each image series may be interleaved and alternatively displayed in a first comparison pane of the display device, while the second image of each image series may be interleaved and alternatively displayed in a second comparison pane of the display device, and so on. For example, if the image series to be interleaved are series A comprising images A1, A2, and series B comprising images B1,B2, the system may generate a first interleaved series ordered A1, B1, and a second interleaved image series ordered A2, B2. In one embodiment, images from each from each of the first and second interleaved image series are concurrently displayed on a display device in separate comparison panes. In one embodiment, an option on the interleave menu, discussed above, may be selected in order to initiate generation of multiple interleaved image series and concurrent display of multiple comparison panes on the display device. In one embodiment, more than two images of image series may be interleaved in the above-described manner and more than two comparison panes may be displayed concurrently on a display device for viewing the generated interleaved image series.

Figure 10:
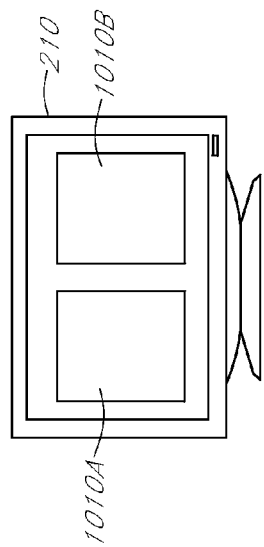
FIG. 10 is a diagram illustrating a display device displaying two comparison panes.

FIG. 10 is a diagram illustrating the display device 210 having two comparison panes 1010A, 1010B. As noted above, multiple interleaved image series may be concurrently displayed on the display device 210 in separate comparison panes. In another embodiment, the display device 210 displays three or more comparison panes for concurrently displaying three or more interleaved image series.

Figure 12:
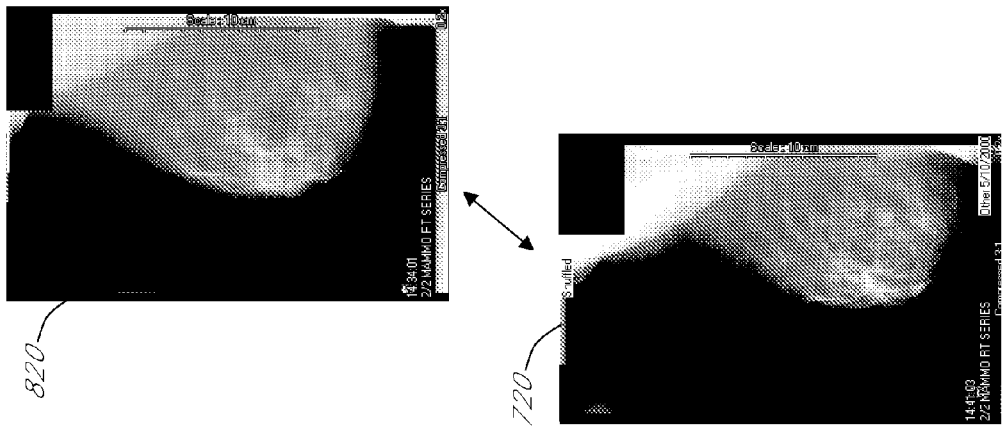
FIG. 12 illustrates the second images of the first and second image series illustrated in FIGS. 7B and 8B interleaved for alternative viewing in a comparison pane.
Figure 11:
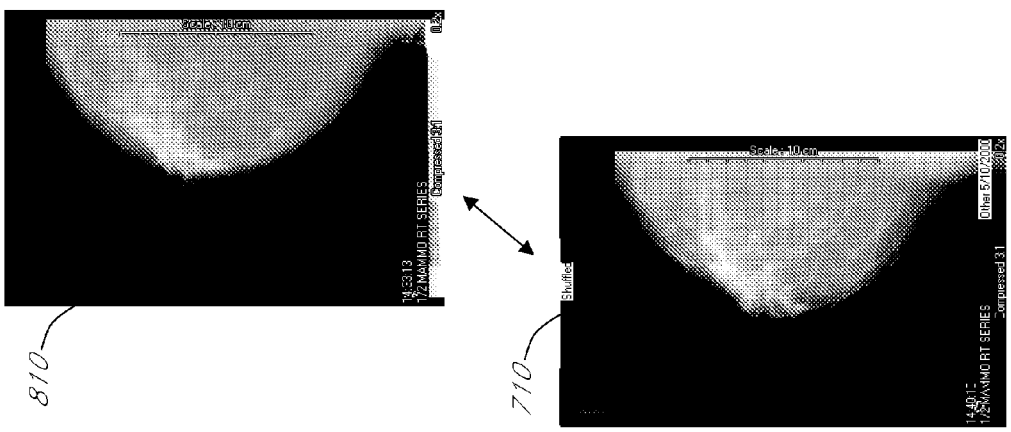
FIG. 11 illustrates the first images of the first and second image series illustrated in FIGS. 7A and 8A interleaved for alternative viewing in a comparison pane.

FIG. 11 illustrates the first images 710, 810 of the first and second image series illustrated in FIGS. 7A and 8A and FIG. 12 illustrates the second images 720, 820 of the first and second image series illustrated in FIGS. 7B and 8B. The images 710, 810 (FIG. 11) comprise a first interleaved image series, while the images 720, 820 (FIG. 12) comprise a second interleaved image series. In the embodiment illustrated in FIGS. 11 and 12, the images 710, 720 are from a first exam and the images 810, 820 are from a second exam. However, the first selected images from each exam, e.g., images 710, 810, are of a first projection, while the second selected images from each exam, e.g., 720, 820, are of a second projection. Thus, it may be advantageous for an interpreter of the images to view the images of the same projection, from different exams, in separate interleaved image series. Accordingly, in the embodiment of FIGS. 10, 11, and 12, a first interleaved image series comprising images 710, 810 are viewed in a first comparison pane 1010A while a second interleaved image series comprising images 720, 820 are viewed in a second comparison pane 100B. In this embodiment, the viewer may advantageously move between images of the same projection in a comparison pane in order to identify differences in the images, while also viewing images of one or more additional projections in additional comparison panes. In one embodiment, any number of images may be included in each of the interleaved images series displayed in comparison panes 101A, 1010B, and additional comparison panes may be concurrently displayed on the display device 210.

The foregoing description details certain embodiments of the invention. It will be appreciated, however, that no matter how detailed the foregoing appears in text, the invention can be practiced in many ways. As is also stated above, it should be noted that the use of particular terminology when describing certain features or aspects of the invention should not be taken to imply that the terminology is being re-defined herein to be restricted to including any specific characteristics of the features or aspects of the invention with which that terminology is associated. The scope of the invention should therefore be construed in accordance with the appended claims and any equivalents thereof.

What is claimed is:

1. A method of viewing medical images from two or more image series on a display device, the method comprising:
   selecting a first image series comprising two or more medical images obtained at a first time;
   selecting at least one comparison image series, each of the comparison image series comprising two or more medical images obtained at a second time;
   interleaving images of the first image series and the comparison image series in order to form an interleaved image series with corresponding medical images from each of the first image series and the comparison image series adjacent to one another in the interleaved image series; and
   sequentially displaying the images of the interleaved image series at a single location on the display device, wherein the method is performed by a computing system comprising one or more computing devices.

2. The method of claim 1, wherein the single location on the display device comprises a comparison pane.

3. The method of claim 1, further comprising selecting a starting image in one or more of the first and comparison image series, wherein the starting images indicate respective first images from the one or more first and comparison image series that are to be included in the interleaved image series.

4. The method of claim 3, further comprising selecting a zoom level for each of the medical images in the first image series by adjusting a zoom level on one of the medical images of the first image series.

5. The method of claim 4, further comprising selecting a zoom level for each of the images in the comparison image series by adjusting a zoom level on one of the medical images of the respective comparison image series.

6. The method of claim 3, further comprising selecting a display characteristic of the images in the first image series by adjusting the display characteristic on one of the medical images of the first image series.

7. The method of claim 3, further comprising automatically selecting a display characteristic of the images in the first image series according to differences in the display characteristics of the images detected by the computing device.

8. The method of claim 1, wherein selecting the at least one comparison image series is performed by the computing device based on predefined comparison rules.

9. The method of claim 8, wherein the predefined comparison rules indicate that image series with substantially the same name as a name of the first image series are selected for comparison with the first image series.

10. The method of claim 8, further comprising:
    displaying a list of image series identifiers associated with one or more image series that satisfy the comparison rules; and
    selecting one or more of the image series identifiers, wherein the image series associated with the selected image series identifiers are selected as comparison image series.

11. The method of claim 1, wherein the sequentially displaying is controlled by an input device coupled to the computing device so that when a predetermined input is received by the computing device, the image displayed at the single location is replaced by an adjacent image in the interleaved image series.

12. The method of claim 11, wherein the predetermined input comprises moving a scroll bar on a mouse.

13. The method of claim 1, further comprising displaying information regarding the medical image currently displayed at the single location.

14. A method of viewing a series of medical images on a display device, the method comprising:
    (a) selecting a first image series comprising a plurality X of medical images of a first portion of an individual obtained at a first time;
    (b) selecting a second image series comprising a plurality Y of medical images of the first portion of the individual obtained at a second time;
    (c) displaying at a predetermined location on the display device a Nth image of the first image series;
    (d) replacing the Nth image of the first image series with a Mth image of the second image series at the predetermined location, wherein the Nth image of the first image series and the Mth image of the second image series depict a corresponding anatomy of the individual at the first and second times, respectively;
    (e) incrementing or decrementing N and M; and
    (f) repeating steps (c) to (e), wherein the method is performed by a computing system comprising one or more computing devices.

15. The method of claim 14, further comprising displaying a user interface on the display device, wherein the predetermined location comprises a comparison pane within the user interface.

16. The method of claim 15, wherein the values of N and M are selected by a user of the computing device.

17. The method of claim 14, wherein the medical images comprise at least one of X-ray, mammogram, MRI, radiograph, computed tomography, magnetic resonance imaging, Ultrasound, positron emission tomography scan, angiogram, and nuclear scan images.

18. The method of claim 14, further comprising:
selecting a third image series for viewing, the third image series comprising a plurality Z of medical images;
replacing the Mth image of the second image series with a Lth image of the third image series at the predetermined location; and
incrementing or decrementing L.

19. The method of claim 14, wherein timing of the steps of displaying and replacing is controlled by an input device to the computing system, wherein the user may determine a speed at which images from the first and second image series are alternatively displayed at the predetermined location using the input device.

20. The method of claim 19, wherein the input device comprises at least one of: a mouse, a trackball, and a keyboard.

21. A computerized method comprising:
transmitting from a computing device to a display device data associated with two or more image panes, each depicting an image from a respective image series;
receiving at the computing device selections of at least two image panes from an input device, in response to said receiving, interleaving by the computing device the images of the image series associated with the selected at least two selected image panes in order to form an interleaved image series having corresponding images from the at least two selected image series adjacent to one another; and
initiating by the computing device display of an image of the interleaved image series in a comparison pane on the display device.

22. The method of claim 21, wherein a user of the computing device selects the image panes by clicking a mouse button after moving a pointer onto each of the image panes.

23. The method of claim 21, wherein a user of the computing device selects the image panes by clicking a mouse button after moving a pointer onto a border between the image panes.

24. The method of claim 21, wherein the comparison pane covers substantially all of a display area of the display device.

25. The method of claim 21, wherein the comparison pane is sized substantially equal to a size of the image panes.

26. The method of claim 21, wherein the displaying step comprises displaying from 2 to 40 image panes.

27. A method of viewing medical images from two or more image series on a display device coupled to a computing device, wherein the method is performed by the computing device, the method comprising:
automatically selecting at least two comparison image series based on predefined user rules, wherein the at least two comparison image series were obtained at different times;
interleaving images of the at least two comparison image series in order to form an interleaved image series with corresponding images from each of the first image series and the comparison image series adjacent to one another in the interleaved image series; and
sequentially displaying the images of the interleaved image series in a comparison pane on the display device.

28. The method of claim 27, wherein the user rules define criteria for selecting image series for comparison.

29. The method of claim 27, wherein the user rules include criteria related to DICOM header file information associated with medical images, wherein comparison image series are selected according to DICOM header file information.

30. A method of viewing medical images from two or more image series on a display device, wherein the method is performed by a computing system comprising one or more computing devices, the method comprising:
selecting a first image series comprising two or more medical images obtained at a first time;
selecting at least one comparison image series obtained at a second time, each of the comparison image series comprising two or more medical images;
interleaving images of the first image series and the comparison image series in order to form two or more interleaved image series with corresponding images from each of the first image series and the at least one comparison image series adjacent to one another in the respective interleaved image series; and
sequentially displaying the images of each of the interleaved image series in corresponding two or more comparison panes that are concurrently displayed on the display device.

31. The method of claim 30, wherein images in each respective interleaved image series are each of a particular projection so that a first interleaved image series comprises images of a first projection and a second interleaved image series comprises images of a second projection.

* * * * *